(12) United States Patent
Johnsen

(10) Patent No.: US 9,341,607 B2
(45) Date of Patent: May 17, 2016

(54) COMPOSITIONS FOR TESTING SMOKE DETECTORS

(75) Inventor: Montfort A. Johnsen, Danville, IL (US)

(73) Assignee: HSI Fire & Safety Group, LLC, Elk Grove Village, IL (US)

( * ) Notice: Subject to any disclaimer, the term of this patent is extended or adjusted under 35 U.S.C. 154(b) by 352 days.

(21) Appl. No.: 13/437,867

(22) Filed: Apr. 2, 2012

(65) Prior Publication Data

US 2013/0111970 A1     May 9, 2013

Related U.S. Application Data

(60) Provisional application No. 61/556,676, filed on Nov. 7, 2011.

(51) Int. Cl.
   *C09K 3/00* (2006.01)
   *G01N 33/00* (2006.01)

(52) U.S. Cl.
   CPC .................................. *G01N 33/007* (2013.01)

(58) Field of Classification Search
   CPC .............................. G01N 33/00; G01N 3/007
   USPC .............. 436/9; 73/1.06; 252/408.1; 340/628
   See application file for complete search history.

(56) References Cited

U.S. PATENT DOCUMENTS 5,785,891 A * 7/1998 Lim .................................. 516/7
2013/0098396 A1* 4/2013 Lousenberg et al. .............. 134/6

OTHER PUBLICATIONS

Knopeck et al., Pushing the Envelope, May 2011, Spray Technology & Marketing Magazine.*
Knopek and Rittinger, Pushing the Envelope, May 2011, Spray Technology & Marketing Magazine, United States.

* cited by examiner

*Primary Examiner* — Jill Warden
*Assistant Examiner* — Julie Tavares
(74) *Attorney, Agent, or Firm* — Freeborn & Peters LLP

(57) ABSTRACT

A composition of matter is provided for testing smoke detectors. The composition includes an oligopolymeric siloxane and a fluorinated, propene-based propellant. The composition is non-flammable under all reasonably foreseeable conditions of use. The oligopolymeric siloxane may comprise phenyl trimethicone (INCI) (International Cosmetic Ingredient Dictionary and Handbook), as typified by Dow Corning 556 Cosmetic Grade Fluid, Dow Corning 558 Fluid and equivalent siloxane compounds. The fluorinated propene-based propellant may comprise trans 1,3,3,3-tetrafluoroprop-1-ene. The trans 1,3,3,3-tetrafluoroprop-1-ene may comprise Honeywell Fluorine Products Division's HFO1,2,3,4ze(E) product. The fluorinated propene-based propellant may be present at from about 94% to 99% by weight. The oligopolymeric siloxane may be present at from about 1% by weight to about 6.0% by weight, ideally 1.5% to 2.0% by weight. Up to about 25% by weight of the composition is may comprise a totally non-flammable propellant or diluent, such as 1,1,1,2-tetrafluoroethane or cis/trans 1,1,1,4,4,4-hexafluorobut-2-ene or iodotrifluoromethane (CIF3).

18 Claims, 3 Drawing Sheets

COMPOSITIONS FOR TESTING SMOKE DETECTORS

CROSS-REFERENCE TO RELATED APPLICATIONS/INCORPORATION BY REFERENCE

This application makes reference to, claims priority to, and claims the benefit of U.S. Provisional Application Ser. No. 61/556,676, filed on Nov. 7, 2011.

The above referenced application is hereby incorporated herein by reference in its entirety.

FIELD OF THE INVENTION

This invention generally relates to smoke detectors. More specifically, this invention relates to novel compositions of matter for testing smoke detectors.

BACKGROUND OF THE INVENTION

Self-pressurized (aerosol) dispensers for the testing of smoke detectors have been marketed for decades. They were originally formulated with about 1 to 4% by weight of some proprietary ingredient and 96% to 99% by weight of a totally or essentially non-flammable propellant such as CFC-12 (dichlorodifluoromethane). When all the CFC aerosol propellants were banned as of 1 Apr. 1978 the fledgling smoke detector tester industry was forced to use either an essentially non-flammable blend of HCFCs (hydrochlorofluorocarbons) or the intensely flammable hydrocarbon propellants, such as propane and iso-butane. The HCFC propellants were banned in 1990, leaving the industry with no other recourse than to use the hydrocarbon propellants.

In 1995 DuPont commercialized totally non-flammable HFC-134a (1,1,1,2-tetrafluoroethane), primarily as a replacement for the CFC-12, still permitted for use in MDIs (Metered Dose Inhalants). Most marketers of smoke detector tester aerosols began to use this new propellant, since it was safer to use in environments where free flames or electrical sparks could be present and cause ignition of the spray. However, HFC-134a is a remarkably poor solvent, and some marketers included up to about 20% by weight of ethanol in their formulas as a co-solvent to solubilize their various "synthetic smoke" active ingredients. Some of these formulas then became marginally flammable—unable to pass standard gas-air flammability tests.

During the late 1990s HFC-134a was accused of having a large GWP (global warming potential). It was shown to be about 1350 times more potent than carbon dioxide in this respect. Under the increasingly critical demeanor of the United States Environmental Protection Agency ("U.S.EPA") and several non-governmental organizations ("NGOs"), HFC-134a suppliers created inter-disciplinary committees that would either approve, approve in limited quantities, or disapprove the sale of this product to marketers, according to product type, annual consumption and other factors. Companies manufacturing products demonstrating health and life safety attributes had the best chance of obtaining HFC-134a. On that basis firms marketing smoke detector testers were permitted to use HFC-134a, while applications by most others were rejected.

In 2008 the State of California passed Senate Bill SA-32 into law. SA-32 was designed to either eliminate or minimize the use of substances demonstrating a significant global warming potential (such as HFC-134a) on an urgent basis. The charge of implementing SA-32 was assigned to California Air Resources Board ("CARB") by Governor Arnold Schwarzenegger. According to Consumer Specialty Products Association ("CSPA") documents CARB has now banned about 85% of the annual tonnage of HFC-134a used in California for duster aerosols. This has caused the affected marketers to reformulate, typically replacing the HFC-134a with HFC-152a (1,1-difluoroethane), which is flammable, but with less intensity than the flammability of the hydrocarbon propellants, such as propane and iso-butane blends.

Meanwhile, the U.S.EPA is slowly developing a very complex program for the step-wise reduction of HFC-134a and similar "high global warmer" gas-liquids, typically used in aerosols, air-conditioner and freezer coolants, foamants and other products, unless exempted. The U.S.EPA has announced that their first reduction, to about 83% of the tonnage used in their reference year of 2005, will be finalized soon. Further reductions will follow, ultimately leading to a complete phase out.

Until quite recently this left the marketers of smoke detector tester aerosols in a difficult position, since only the intensely flammable hydrocarbon propellants could be used without present or future restraints. Since industrial smoke detectors are sometimes located in areas where free flames and spark producing electrical motors, switches and similar equipment are present the spraying of aerosol formulations typically containing 96 to 99% by weight of intensely flammable hydrocarbon propellants could create a considerable risk to life safety.

For completeness, there is another propellant, called dimethyl ether, which is also quite flammable. It is a very strong solvent and has not been seriously considered for smoke detector testers due to concerns about its ability to gradually erode plastic components of the detector.

During the year 2010 the aerosol industry recognized that Honeywell Fluorine Products was developing a new, non-flammable aerosol propellant. On or about May 8, 2011, an article in the ST&M (Spray Technology and Marketing) journal provided documentation. The propellant was HFO1234ze (E) (trans 1,3,3,3-tetrafluoroprop-1-ene) having a negligible GWP and almost completely non-flammable. It was particularly offered as a replacement for HFC-134a and HFC-152a used in duster aerosols, where it would constitute from about 99.5 to 100.0% of these formulas. It has been considered as an essential formula ingredient of the subject invention, if modified so that it would become totally non-flammable.

US regulators have a long history of applying certain test procedures and pass/fail criteria to aerosols, primarily used for the warning labels of aerosols and marking of outer shipping cartons. For example, the Flame Propagation Test, used by the United States Consumer Products Safety Commission ("U.S.CPSC"), the U.S.EPA, and the United States Department of Transportation ("U.S.DOT") (formerly), requires that the aerosol be first equilibrated to 70° F., and then sprayed through the top third of a candle flame from a distance of six inches. If the spray ignites, forming a fire plume longer than 18 inches from the candle, then dispensers of that product must be labeled as "Flammable," provided they are larger than four fluid ounces (118.2 mL) in capacity. This does not mean that products passing this test may be labeled as "Non-Flammable". Quite often they may have a lesser degree of intrinsic flammability.

A second test is the Closed Drum Test (in Europe, the Enclosed Space Test). While currently obsolete in the USA, it is currently used in Europe, Japan, by other nations, and by certain international transportation organizations, such as International Maritime Consultative Organization ("IMCO"). In the interest of global harmonization of aerosol labeling and shipping, both the (Federation of European Aerosol Associations—17 countries) and the United Nations are seeking to re-establish this test in the USA. The test consists of spraying a fixed amount of the aerosol product into a 55 U.S. gallon steel drum or similar vessel, which contains a lit candle or gas burner. One end of the drum is covered with a thin film of polyethylene. If the Lower Flammable Limit ("LFL") is reached, a large volume of flame will be produced, normally accompanied by a "whooshing" sound and with heat and pressure sufficient to rupture the film. Here again there will be aerosol products that will pass the test, but would fail it if more product had entered the drum. Aerosols that pass the test must not be labeled as "Non-Flammable", but may be labeled as "Non-Flammable by the Closed Drum Test", or the equivalent. Even these modified warnings can lead to consumer confusion and possible misuse of the product.

A listing of the official aerosol flammability tests, including those described above, is presented as follows:
The Flame Propagation Test.
The Flashback Test.
The Closed Drum Test.
The Ignition Distance Test (Europe and U.N.).
The Enclosed Space Test (Europe and U.N.)
The Foam Flammability Test (Europe and U.N.)
The U.S. CPSC Open Cup Flash Point Test.
The U.S.EPA Open Cup Flash Point Test.
Other tests have been published, such as the Closed Cup Flash Point test and the 200° C. Preheated Hot Plate Spray Test, but they have no official sanction.

All of these tests are used to differentiate aerosols by their relative flammability. None of the tests, individually or in concert, can be used to qualify an aerosol product as "Totally Non-flammable", "Almost Completely Non-Flammable" or "Non-Flammable". However, in the USA and Canada there are no laws or regulations that would prevent an over-zealous marketer from marking his aerosol product as "Non-Flammable" or the equivalent, provided it passes that country's applicable, official tests. The primary deterrent for companies marketing such products is being accused of "failure to warn" or "misleading labeling" in the event of an accident. A secondary deterrent is that the U.S.FTC (U.S. Federal Trade Commission) may consider such products to be labeled with a false advertising statements.

In the USA the only test for establishing "Non-Flammability" is the ASTM E-681 (American Society for Testing Materials, Method E-681) assay. The procedure utilizes a five liter (c.a. 1.2 U.S. gallon) flask with an enclosed sparking device. Precisely measured amounts of the aerosol product are introduced, with intermittent operation of the sparking unit. If no flame propagation occurs the product is deemed "Non-Flammable". The test is typically conducted at 68° F. Flammability is said to occur if a flame is produced that reaches the wall of the container. It must also exhibit an angle of greater than 90° from the spark source. These effects must occur at a gas concentration of less than 12 volume-percent for the product to be considered "Flammable". The term "gas", as used in this test, means a fluid with a boiling point of 68° F. or lower, under an atmospheric condition of 760 mm. of mercury absolute pressure.

The lowest concentration of gas that produces the above flame propagation is recorded as the LFL. The highest concentration of gas that still produces the above flame is recorded as the Upper Flammable Limit ("UFL"). The terms LEL and UEL are often used interchangeably with LFL and UFL, resp. The "E" stands for "Explosive". The "window of flammability" between the LFL and UFL is described as the "vapor flame limits" or "flammable range". Gases that exhibit a flammable range at 68° F. are considered to be "Flammable" by this test. Conversely, a gas that fails to exhibit an LFL and UFL at 68° F. by this test is considered as "Non-Flammable".

The European counterpart to the ASTM E-681 is the EU A11 test. The apparatus consists of a two-inch inside diameter by 12 inch long glass tube with an internal ignition source composed of an electrical sparking device that lights a match. The assessment criteria are similar to those that are applied to the ASTM E-681 method.

As is known to those skilled in this area, the flammable proclivity of gases increases as the temperature increases, as the pressure is increased, and sometimes changes as gaseous impurities are added or increased. To our knowledge and belief no information has been published regarding the effect, if any, of adding an essentially non-volatile liquid to the test aerosol dispenser. As a classic example of the pressure effect, HFC-134a is totally non-flammable at 68° F. and 760 mm mercury absolute pressure. But at 68° F. and a pressure of about 1550 mm mercury absolute (15 psi-gauge) it displays a flammable range starting at about 7.5 volume-percent gas.

To more fully define the flammability profile of their HFO1234ze(E) propellant Honeywell tested it using both the ASTM E-681 and European EU A11 test methods. Testing was also performed at several temperatures. The USA testing was conducted by Honeywell, while the European method of testing was done by Chilworth Technology U.K. (in England), a highly regarded flammability testing firm. Results were provided by Honeywell as follows:
Method ASTM E-681
At 68° F. No flammability. (No LFL or UFL.)
At 86° F. LFL=7.7 volume-% and UFL=8.7 volume-%.
At 140° F. LFL=5.8 volume-% and UFL=11.3 volume-%.
At 212° F. LFL=5.8 volume-% and UFL=11.8 volume-%.
Method EU A11
At 73° F. No flammability. (No LFL or UFL.)
At 212° F. LFL=7 volume-% and UFL=12 volume-%

FIG. 1 is a graphic representation of the above test results, which is hereby made a part of this patent application. Specifically, FIG. 1 shows that propellant HFO1234ze(E) can produce a potentially flammable gas-air mixture above a temperature of about 79° F. when tested by a standard method identified as ASTM E-681. In the graph (100) indicates the LFL arm, while (101) indicates the UFL. The area enclosed by the parabolic graph contains flammable gas-air compositions at the indicated temperatures. (102) depicts a typical experimental result. There are four of these on the graph and two more are indicated at higher temperatures. (103) indicates that all gas-air compositions below about 79° F. are non-flammable.

One may conclude from this rather intensive testing that Honeywell's HFO1234ze(E) begins to develop a flammable range at about 79 to 80° F. The range rapidly increases with rising temperature.

Whenever an aerosol is sprayed the gaseous content of the spray becomes increasingly diluted with ambient air. The gas concentration ranges from essentially 100% at or very close to the spray actuator terminal orifice, moving ultimately down to essentially 0% when fully diluted with air. During the spraying episode some parts of the spray may be ephemerally diluted into the critical area such as of from 7.7 to 8.7 volume-percent at 86° F. If the temperature is 80° F. or higher, and a suitable ignition source is present, then a flammable event becomes possible, perhaps with serious consequences. The relative fire hazard increases at higher temperatures, since the flammability range broadens Further limitations and disadvantages of conventional and traditional aerosol systems will become apparent to one of ordinary skill in the art through comparison of such systems with the present invention described herein.

BRIEF SUMMARY OF THE INVENTION

A system and/or composition is provided for testing smoke detectors substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a system and/or composition for testing smoke detectors. Exemplary embodiments of the invention may comprise a composition of matter for testing smoke detectors, which includes an oligopolymeric siloxane and a fluorinated, propene-based propellant. The composition is non-flammable under all reasonably foreseeable conditions of use. The oligopolymeric siloxane may comprise phenyl trimethicone (INCI) (International Cosmetic Ingredient Dictionary and Handbook), as typified by Dow Corning 556 Cosmetic Grade Fluid, Dow Corning 558 Fluid and equivalent siloxane compounds.

The fluorinated propene-based propellant is trans 1,3,3,3-tetrafluoroprop-1-ene. The trans 1,3,3,3-tetrafluoroprop-1-ene is a HFO1,2,3,4ze(E) product, such as Honeywell Fluorine Products Division's HFO1,2,3,4ze(E) product. The fluorinated propene-based propellant may be present at from about 94% to 99% by weight. The oligopolymeric siloxane may be present at from about 1% by weight to about 6.0% by weight, ideally 1.5% to 2.0% by weight. Up to about 25% by weight of the composition may comprise a totally non-flammable propellant or diluent, such as 1,1,1,2-tetrafluoroethane (such as DuPont's HFC-134a), or cis/trans 1,1,1,4,4,4-hexafluorobut-2-ene (such as DuPont's HFO1336mzz), or iodotrifluoromethane ($CIF_3$).

Another embodiment of the invention provides a self-pressurized aerosol packaging system, comprising a composition of matter for testing smoke detectors, such as the compositions disclosed above.

Another embodiment of the invention provides a method for testing a smoke detector. The method may comprise spraying a composition on the smoke detector, and waiting for said smoke detector to go off. The composition may be substantially as described above. The composition may be sprayed with an aerosol dispenser held vertically or at an angle to the smoke detector, depending on the height of the smoke detector above floor level. The composition may be sprayed onto the smoke detector from a specified distance, typically 1 to 4 feet.

Figure 1:
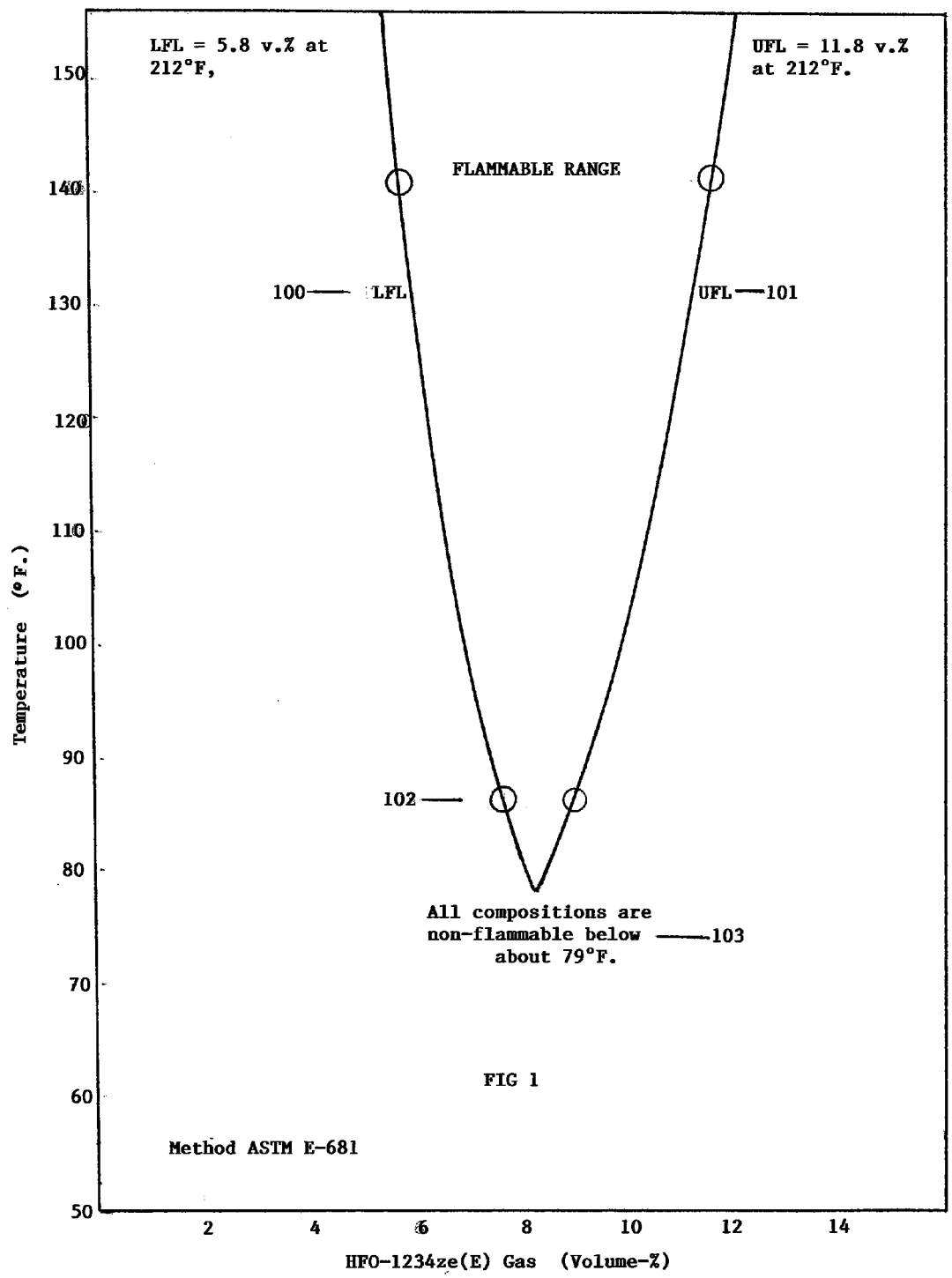
FIG. 1 is a graphic representation that illustrates the temperatures at which flammable ranges exist for 100% trans 1,3,3,3-tetrafluoroprop-1-ene.
Figure 2:
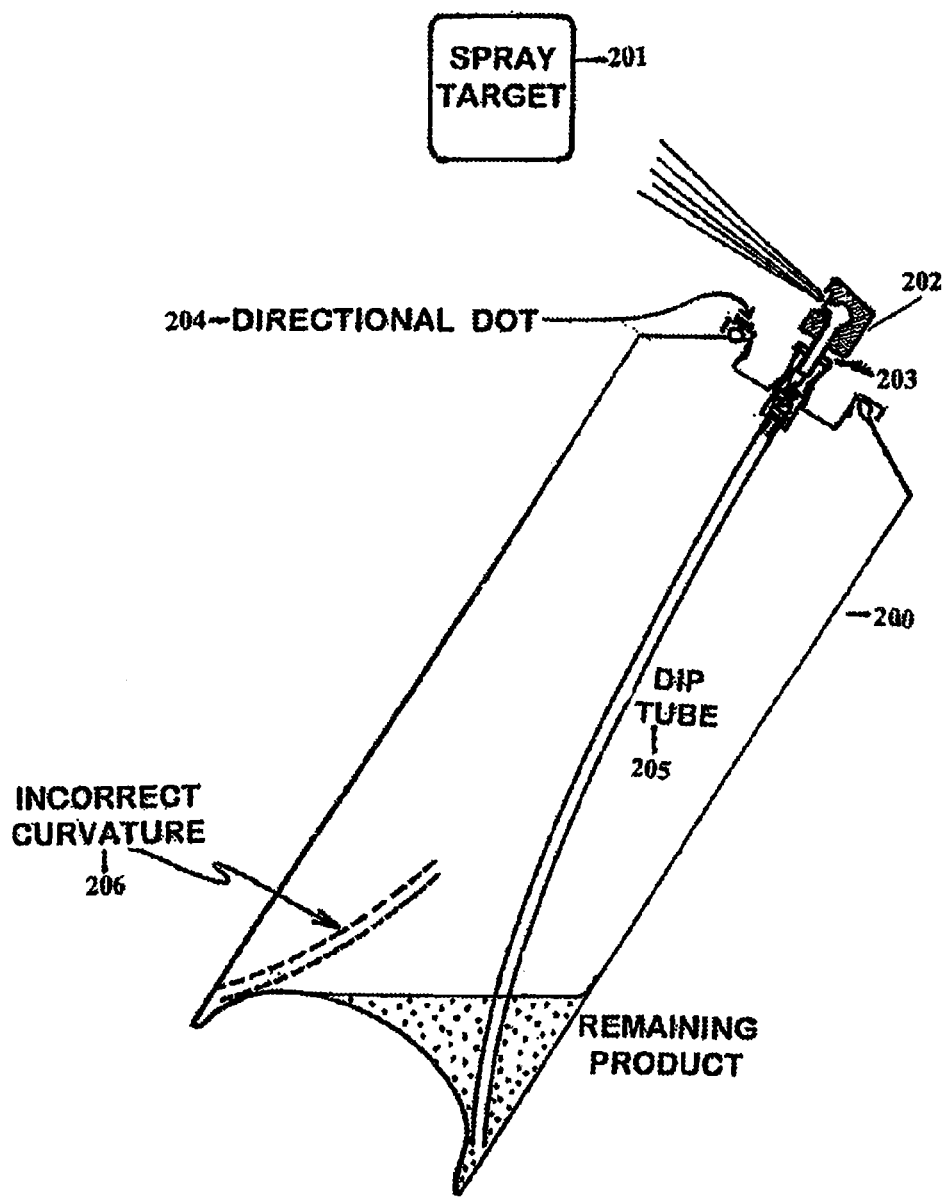
FIG. 2 is a cross-sectional view of an aerosol tilted an angle for spraying a smoke detector mounted on a ceiling, showing the dip tube extending into the liquid portion of the can, in accordance with an embodiment of the invention.
Figure 3:
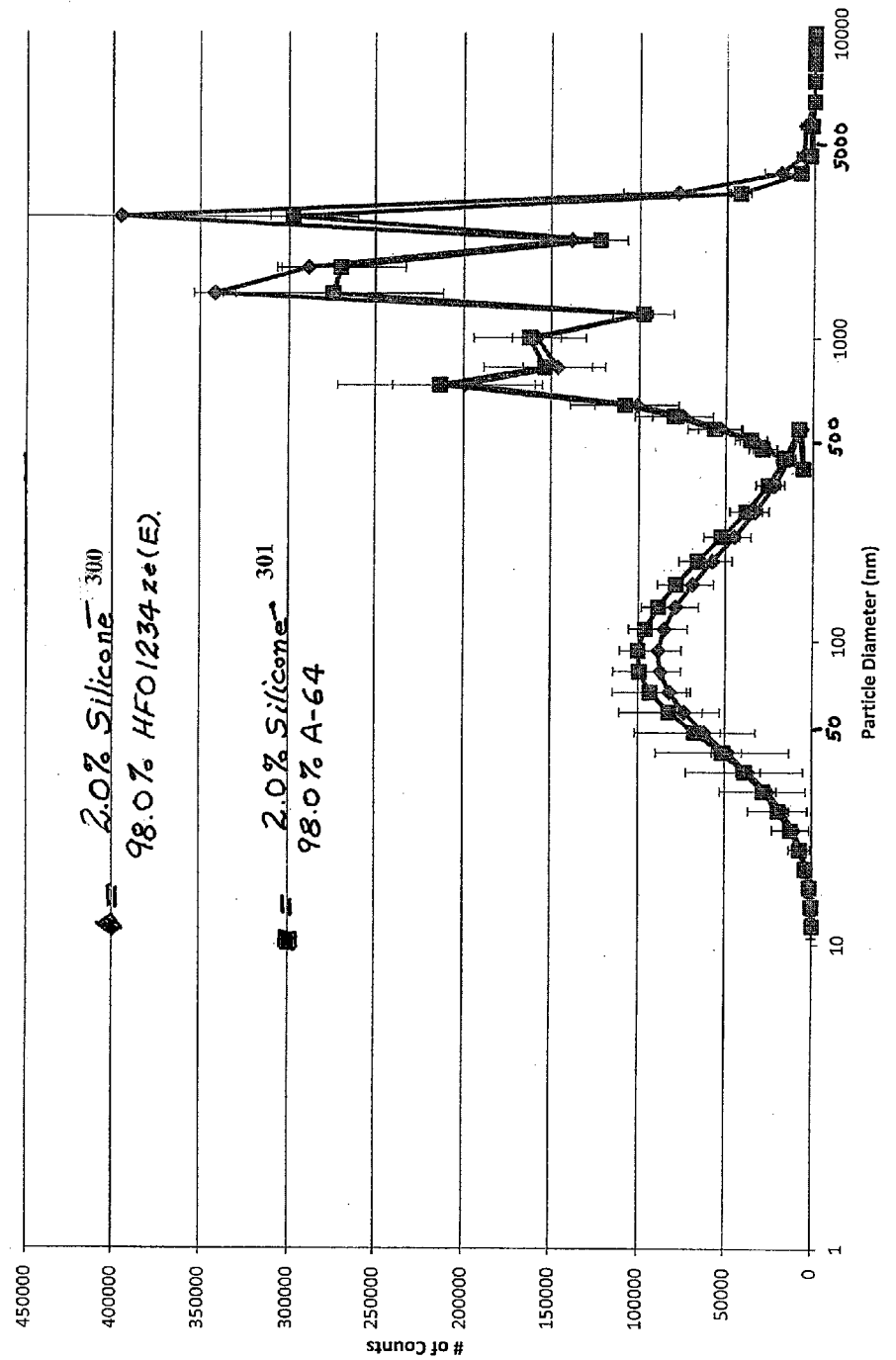
FIG. 3 is a graph showing that the particle size distribution of the 2.0% siloxane and 98% HFO 1234ze(E) formulation has the correct attributes needed to properly test smoke detectors, in accordance with an embodiment of the invention.

FIG. 2 is a cross-sectional view of an aerosol dispenser (200) tilted at an angle for spraying the composition on a smoke detector mounted on a ceiling, showing the dip tube (205) extending into the liquid portion of the can, in accordance with an embodiment of the invention. (201) illustrates the spray target (usually a smoke detector), actually at a greater distance from the dispenser than is depicted in the FIG. 2. The effect of tilting the aerosol dispenser is illustrated by the cross-sectional drawing in FIG. 2, showing that the end of the valve dip tube must always be within the liquid, or the aerosol will emit only gas. This is done by having the valve supplier align the curvature of the dip tube 180 degrees from the position of a directional dot (204), placed on the crown of the valve mounting cup by the use of a magic marker or an equivalent instrument. The directional dot is found on numerous aerosol dispensing products. The valve actuator (202) is then manually or automatically aligned to spray over the dot. In this manner all the liquid product may be discharged. Right beneath the valve actuator is the container valve (203), which is hermetically sealed to the container during the filling process. For completeness, FIG. 2 also illustrates an incorrect dip tube position (206), whereby the valve can only discharge the gaseous propellant. After spraying the smoke detector for a certain distance and duration the detector will sound an alarm identical to that which occurs when the smoke detector detects actual smoke.

Another embodiment of the invention provides a method for making a composition of matter for testing smoke detectors. The method may comprise combining an oligopolymeric siloxane and a fluorinated propene-based propellant to produce the composition such that the composition is totally non-flammable under all reasonably foreseeable conditions of use. The composition may be substantially as described above.

The composition is utilized to verify the continuing ability of smoke detectors to sound an alarm whenever the smoke detector is impacted by smoke. Spraying the composition onto a smoke detector simulates the detection of smoke by the smoke detector.

The subject invention describes compositions of matter suitable for rendering Honeywell's HFO1234ze(E) aerosol propellant totally non-flammable under all reasonably foreseeable conditions of industrial or domestic use. It involves the incorporation of about 1.5 to 2.0% by weight of an oligopolymeric siloxane, such as phenyltrimethicone (INCI) into the propellant, in which it is readily soluble up to at least 10% at 70° F. This siloxane, produced as a mixture of monomeric, dimeric and trimeric molecules (CAS #2116-84-9, et al.) exhibits a Tagliabue Closed Cup Flash Point of about 215° F. and may be considered as a Class IIIB Combustible Liquid, with reference to the NFPA (National Fire Protection Association) Manual NFPA 30. The preferred product is available from the Dow Corning Corporation as "Dow Corning 556 Cosmetic Grade Fluid", a clear, colorless, odorless, slightly viscous liquid. "Dow Corning 558 Fluid" has essentially the same composition and there are a number of other suppliers.

It is now necessary to define the different [levels] of flammability, as used here, and to mention certain tests and test results for HFO1234ze(E) that relate directly to this invention.

Totally Non-Flammable: An aerosol product whose vapors cannot produce a flame propagation in air at ambient temperatures; i.e. below 104° F., when tested by the ASTM E-681 method or in Europe by the very similar EU A11 test; but which passes all other official tests designed to control labeling of aerosols or their outer shipping containers.

Almost Completely Non-Flammable: An aerosol product whose vapors can produce a flame propagation in air at ambient temperatures (typically 50 to 104° F.) when tested by the ASTM E-681 method or in Europe by the very similar EU A11 test; but which passes all other official tests designed to control labeling of aerosols or their outer shipping containers.

Non-Flammable: An aerosol product whose vapors can produce a flame propagation in air at below ambient temperatures (typically below 50° F.), when tested by the ASTM E-681 method or (in Europe) by the very similar EU A11 test; but which passes all other official tests designed to control labeling of aerosols or their outer shipping containers. For example, when sprayed upon the top of a candle flame from a distance of six inches, no flame extension is noted.

Marginally Flammable: An aerosol that passes the official tests designed to control labeling of aerosols and their outer shipping containers, but, when sprayed upon the top of a candle flame from a distance of six inches a minor extension (less than 10 inches) of the flame is noted.

Flammable: An aerosol that fails any of the official tests designed to control labeling of aerosols and their outer shipping containers.

Extremely Flammable (Intensely Flammable): An aerosol that fails the "Extremely Flammable" criteria of certain official tests designed to control labeling of aerosols and their outer shipping containers.

Dow Corning 556 Cosmetic Grade Fluid currently enjoys the protection of U.S. Pat. Nos. 5,785,891 and 5,139,699 for its use at about 2% by weight in formulas designed to check the continuing satisfactory operation of smoke detectors. The primary objective of this patent application is to utilize this product in creating a totally non-flammable smoke detector tester composition. However, it may also be utilized beneficially for such other aerosol products as totally non-flammable boat horns, various totally non-flammable surface chilling sprays, totally non-flammable hair glosses, totally non-flammable lubricants and other aerosol products that benefit from the health and life safety aspects of total non-flammability.

In one aspect of the invention the addition of about 2% by weight of phenyltrimethicone to about 98% by weight of HFO1234ze(E) produces a solution that, when tested by the standard ASTM E-681 method, is totally non-flammable even at the elevated temperature of 104° F., and probably even higher. This unanticipated result shows that phenyl-trimethicone, which is combustible, acts to quench the flammability of HFO1234ze(E) even at this elevated temperature. Other tests have also shown that the solution is effective in the testing of smoke detectors.

FIG. 3 is a graph produced by Underwriter's Laboratories, Inc. (UL) showing that the particle size distribution of the 2.0% siloxane and 98% HFO 1234ze(E) formulation has the correct attributes needed to properly test smoke detectors, in accordance with an embodiment of the invention. Smoke particle size and count distribution was characterized using a Model WPS 1000XP wide range particle size spectrometer from MSP Corporation of Shoreview, Minn. The WPS spectrometer combines laser light scattering, electrical mobility and condensation particle counting technologies in a unique, single instrument with the capability of measuring the concentration and size distribution of aerosol particles ranging from 10 nm to 10,000 nm (0.01 μm to 10 μm) in diameter. The instrument divides a 1 Liter/min sample flow between the dynamic mobility analyzer (DMA) and the laser particle spectrometer (LPS) modules to develop the particle size distribution. The DMA module is sensitive to particle sizes ranging from 10 nm to 500 nm (0.01 μm to 0.50 μm), whereas the LPS module is sensitive to particle sizes ranging from 350 nm to 10,000 nm (0.35 μm to 10 μm). Particle sizes were measured by the DMA module at a rate of 2 seconds per size interval (bin). For the data reported herein, the DMA analyzer was set to obtain data for 24 size intervals resulting in an ensemble measurement time of 48 seconds. Particle size measurements by the LPS module are instantaneous, however the recorded count is an average over the 48 second ensemble measurement time. The analyzer was purged between successive ensemble measurements resulting in subsequent measurements being continuously collected at 67 second intervals.

Specifically, FIG. 3 shows a graph abscissa which is logarithmic, with a range of 1 nm (nanometer) to 10,000 nm. The two compositions tested (2% by weight of siloxane to about 98% by weight of HFO1234ze(E)) both showed particles ranging from about 15 to 4500 nm—or from 0.015 to 4.5 microns. Smoke from fires is composed of ash particles in this same range, which is an important attribute in "fooling" the smoke detector during testing episodes. The trace outlined by diamond shaped dots represents the composition 2.0% siloxane and 98% HFO1234ze(E) (300). The trace outlined by square dots represents a commercial smoke detector tester product, having the extremely flammable composition 2.0% siloxane and 98% of a mixture of Propane and iso-Butane, called "A64" (301).

As can be observed from FIG. 3, the two traces are essentially synonymous (i.e., the particle size distribution of the 2.0% siloxane and 98% HFO1234ze(E) composition is essentially identical to that of the commercial formulation). This important finding was an essential criterion in Underwriter's Laboratory's very recent approval of the 2.0% siloxane and 98% HFO1234ze(E) formulation to carry their official seal of approval on product labels and advertising.

The choice of the 104° F. (50° C.) testing temperature is based on the premise that smoke detector testers will virtually never be used at temperatures higher than this. This provides support for the notion that 2% by weight of phenyltrimethicone and 98% by weight of HFO1234ze(E) composition will produce a spray that is totally non-flammable under all reasonably foreseeable conditions of use. Since the aerosol content is a true solution, the preferred ratio of 2:98 will survive until the dispenser is empty. This allows the totally non-flammable attribute to be sustained for the life of the aerosol dispenser.

It is recognized that skilled formulators may attempt to introduce other non-flammable or marginally flammable solvents or propellants to achieve totally non-flammable compositions for testing smoke detectors. These might include 1,2,2,2-tetrafluorethane (HFC-134a), cis/trans 1,1,1,4,4,4-hexafluorobut-2-ene (HFO1336mzz), or iodotrifluoromethane. The HFC-134a would be a very poor choice because it is implicated in regulations designed to reduce and eventually eliminate compounds having a significant global warming potential. Moreover, cis/trans HFO1336mzz and iodotrifluoromethane, while both totally non-flammable, are non-commercial gas-liquids.

To address this situation aerosol products were prepared containing 1.6% by weight of phenyltrimethicone, 23.4% by weight of cis/trans HFO1336mzz and 75.0% by weight of HFO1234mzz(E). A true solution was formed. The product successfully activated smoke detectors and was found to be totally non-flammable at 104° F. by the standard ASTM E-681 test. The slight reduction in phenyltrimethicone was done to better ensure achieving the desired mean aerodynamic particle size of less than about 1 micron, to compensate for the inclusion of the cis/trans HFC1336mzz solvent which had a negligible particle break-up value.

Another aspect of the invention is that both the air-free and vacuum crimped binary and tertiary compositions we have tested produce pressures of less than 160 psi-g. at 130° F. In the USA and Canada these pressures legally permit the use of the "DOT Specification 2P" aerosol can for interstate and inter-province transportation, resp. These aerosol dispensers may legally contain compositions having pressures up to 160 psi-g. at 130° F. The "DOT Specification 2P" container is much less costly than the heavy duty, DOT-exempted dispensers required to legally hold CFC-134a, which has an air-free pressure of about 202 psi-g. at 130° F.

The advantages of the totally non-flammable smoke detector aerosol products include:
1. Ultimate safety in use—including in highly sensitive areas where ignition sources may be present.
2. The use of ingredients that are environmentally friendly—no stratospheric ozone depletion, negligible tropospherric ozone production and a negligible global warming potential.
3. A replacement for CFC-134a, which has an excessive global warming potential and is being phased out. No other totally non-flammable alternative exists.
4. Excellent electronic response of smoke detectors when tested.
5. HFO1234ze(E) is approved by and listed on the U.S. EPA's Toxic Substances Control Act (TSCA) chemical substance inventory and Significant New Aerosol Propellant (SNAP) programs for alternative aerosol propellants. Phenyltrimethicone is also approved by and listed on TSCA.
6. Optionally, up to at least 23.5% by weight of cis/trans HFO13346mzz can be added as a totally non-flammable solvent.
7. In the atmosphere the half-life of HFO1234ze(E) is only about two weeks—not bio-accumulative
8. The proposed commercial aerosol product has been exhaustively tested by Underwriter's Laboratory, Inc. prior to marketing. No impediments were noted.
9. Both phenyltrimethicone and HFO1234ze(E) are listed in the European Registration, Evaluation, Authorisation and Restriction of Chemical substances (REACH) compendium.
10. The addition of 2% by weight of phenyltrimethicone eliminates the flammable range of HFO1234ze(E) up to a temperature of at least 104° F.

The totally non-flammable mixtures of Phenyltrimethicone and HFO1234ze(E) may be used beneficially for other products, such as boat horns and lubricants.

With the forthcoming absence of CFC-134a there will be no other totally non-flammable propellant legally available to the USA, Canadian and European aerosol industries. (These countries represent about 9.3 billion units of the world total of 13.7 billion aerosols per year).

What is claimed is:

1. A composition of matter for testing smoke detectors, the composition comprising:
   about 2% oligopolymeric siloxane and about 98% trans 1,3,3,3-tetrafluoroprop-1-ene; wherein the composition is non-flammable at 104 degrees Fahrenheit at standard atmospheric pressure.

2. The composition of claim 1, wherein the oligopolymeric siloxane is phenyl trimethicone (INCI) (International Cosmetic Ingredient Dictionary and Handbook).

3. A self-pressurized aerosol packaging system, comprising:
   a composition of matter for testing smoke detectors, the composition comprising:
      about 2% oligopolymeric siloxane and about 98% trans 1,3,3,3-tetrafluoroprop-1-ene wherein the composition is non-flammable at 104 degrees Fahrenheit at standard atmospheric pressure; and
   an aerosol dispenser for holding the composition under pressure, the container comprising a valve and an actuator, wherein when used the actuator will open the valve to release the composition and produce a spray;
   wherein said spray may be utilized for periodically testing operation of said smoke detectors.

4. The self-pressurized aerosol packaging system of claim 3, wherein said oligopolymeric siloxane is phenyl trimethicone (INCI) (International Cosmetic Ingredient Dictionary and Handbook).

5. A method for testing the operation of a smoke detector, the method comprising:
   spraying a composition on the smoke detector, wherein the composition comprises:
      about 2% oligopolymeric siloxane and about 98% trans 1,3,3,3-tetrafluoroprop-1-ene wherein the composition is non-flammable at 104 degrees Fahrenheit at standard atmospheric pressure; and
   waiting for said smoke detector to go off to determine if the smoke detector is operational.

6. The method according to claim 5, the method comprising spraying said composition with an aerosol dispenser held vertically or at an angle to said smoke detector.

7. The method according to claim 5, the method comprising spraying said composition onto said smoke detector for about 0.1 to 5 seconds from a distance of about 2 to 4 feet.

8. The method of claim 5, wherein said oligopolymeric siloxane is phenyl trimethicone (INCI) (International Cosmetic Ingredient Dictionary and Handbook).

9. A method for making a composition of matter for testing smoke detectors, comprising:
   combining about 2% oligopolymeric siloxane and about 98% trans 1,3,3,3-tetrafluoroprop-1-ene; wherein the composition is non-flammable at 104 degrees Fahrenheit at standard atmospheric pressure.

10. The method of claim 9, wherein said oligopolymeric siloxane is phenyl trimethicone (INCI) (International Cosmetic Ingredient Dictionary and Handbook).

11. A composition of matter for testing smoke detectors, the composition comprising about 2% oligopolymeric siloxane, about 23% cis/trans 1,1,1,4,4,4-hexafluorobut-2-ene and about 75% trans 1,3,3,3-tetrafluoroprop-1-ene.

12. The composition of claim 11, wherein the composition is non-flammable up to at least 104 degrees Fahrenheit at standard atmospheric pressure.

13. The composition of claim 11, wherein said oligopolymeric siloxane is phenyl trimethicone (INCI) (International Cosmetic Ingredient Dictionary and Handbook).

14. A self-pressurized aerosol packaging system, comprising:
   a composition of matter for testing smoke detectors, the composition comprising:
      about 2% oligopolymeric siloxane, about 23% cis/trans 1,1,1,4,4,4-hexafluorobut-2-ene and about 75% trans 1,3,3,3-tetrafluoroprop-1-ene; and
   an aerosol dispenser for holding the composition under pressure, the container comprising a valve and an actuator, wherein when used the actuator will open the valve to release the composition and produce a spray;

wherein said spray may be utilized for periodically testing operation of said smoke detectors.

15. The self-pressurized aerosol packaging system of claim 14, wherein the oligopolymeric siloxane is phenyl trimethicone (INCI) (International Cosmetic Ingredient Dictionary and Handbook).

16. The self-pressurized aerosol packaging system of claim 14, wherein the composition is non-flammable at standard atmospheric pressure up to at least 104 degrees Fahrenheit.

17. A method for making a composition of matter for testing smoke detectors, comprising:
   combining about 2% oligopolymeric siloxane, about 23% cis/trans 1,1,1,4,4,4-hexafluorobut-2-ene and about 75% trans 1,3,3,3-tetrafluoroprop-1-ene to produce the composition such that the composition is non-flammable at standard atmospheric pressure up to at least 104 degrees Fahrenheit.

18. The method of claim 17, wherein the oligopolymeric siloxane is phenyl trimethicone (INCI) (International Cosmetic Ingredient Dictionary and Handbook).

* * * * *